(12) United States Patent
Mazzone et al.

(10) Patent No.: US 8,912,164 B2
(45) Date of Patent: Dec. 16, 2014

(54) RE-EPITHELIALIZING PHARMACEUTICAL COMPOSITIONS COMPRISING XANTHAN GUM

(75) Inventors: Maria Grazia Mazzone, Catania (IT); Grazia Paladino, Catania (IT); Clara Marino, Catania (IT); Ornella Peri, Catania (IT); Vincenzo Enea, Catania (IT)

(73) Assignee: SIFI S.p.A., Lavinaio, Aci Sant'Antonio (IT)

( * ) Notice: Subject to any disclaimer, the term of this patent is extended or adjusted under 35 U.S.C. 154(b) by 1366 days.

(21) Appl. No.: 10/512,521

(22) PCT Filed: Apr. 24, 2003

(86) PCT No.: PCT/IT03/00257
§ 371 (c)(1),
(2), (4) Date: Jun. 6, 2005

(87) PCT Pub. No.: WO03/092706
PCT Pub. Date: Nov. 13, 2003

(65) Prior Publication Data
US 2005/0234011 A1 Oct. 20, 2005

(30) Foreign Application Priority Data
Apr. 30, 2002 (EP) .................................. 02425274

(51) Int. Cl.
| | | |
|---|---|---|
| *A01N 43/04* | (2006.01) | |
| *A61K 31/715* | (2006.01) | |
| *A61K 9/06* | (2006.01) | |
| *A61K 9/00* | (2006.01) | |
| *A61K 31/723* | (2006.01) | |
| *A61K 47/36* | (2006.01) | |
| *A61K 31/573* | (2006.01) | |

(52) U.S. Cl.
CPC ................ *A61K 31/715* (2013.01); *A61K 9/06* (2013.01); *A61K 9/0048* (2013.01); *A61K 31/723* (2013.01); *A61K 47/36* (2013.01); *A61K 31/573* (2013.01)
USPC .......................................................... 514/54

(58) Field of Classification Search
USPC .......................................................... 514/54
See application file for complete search history.

(56) References Cited

U.S. PATENT DOCUMENTS

| | | | |
|---|---|---|---|
| 4,136,177 A | 1/1979 | Lin et al. | |
| 4,370,324 A | 1/1983 | Bernstein | |
| 4,525,346 A | 6/1985 | Stark | |
| 4,711,780 A * | 12/1987 | Fahim | 424/641 |
| 4,826,872 A | 5/1989 | Terao et al. | |
| 6,406,712 B1 * | 6/2002 | Rolf | 424/445 |
| 6,919,321 B2 * | 7/2005 | Wang et al. | 514/54 |

FOREIGN PATENT DOCUMENTS

| | | | | |
|---|---|---|---|---|
| EP | 0480189 A1 * | 4/1992 | ............ | A61K 31/73 |
| WO | 99/13863 | 3/1999 | | |
| WO | 00/42986 | 7/2000 | | |

OTHER PUBLICATIONS

Ceulemans et al., "The Use of Xanthan Gum in an Opthalmic Liquid Dosage Form: Rheological Characterization of the Interaction with Mucin," 2002, Journal of Pharmaceutical Sciences, vol. 91, pp. 1117-1127.*
Campoli-Richards et al., "Netilmicin: A Review of its Antibacterial Activity, Pharmacokinetc Properties and Therapeutic Use," 1989, Drugs, vol. 38, Issue 5, pp. 703-756.*
Dorigo et al, Collagen Shields Delivery of Netilmicin: A Study of Ocular Pharmacokinetics, 1995, Chemotherapy, 41, pp. 1-4.*
Aragona et al. "Long Term Treatment with Sodium Hyaluronate-Containing Artificial Tears Reducers Ocular Surface Damage in Patients with Dry Eye". Br J Ophthalmol 2002; 86: 181-4.
Paladin et al. "Sodium Hyaluronate Gel in Epithelial Corneal Healing After Alkali-Burn Injury", Investigative Ophthalmology & Visual Science, vol. 38, No. 4, Part 1-2, 1997, p. S406 XP-002214046.
Hwang et al. "Burn Remedial Effects on Rat Skins of Natural Polysaccharide Ointments". J. Korean Ind. Eng. Chem. vol. 11, No. 6, Oct. 2000, pp. 657-661.
Weijtens et al., "High Concentration of Dexamethasone in Aqueous and Vitreous After Subconjuctival Injection," *American Journal of Ophthalmol.*, 128, pp. 192-197, 1999.
Ashford et al., "A Detailed Assessment Procedure of Anti-Inflammatory Effects of drugs on Experimental Immunogenic Uveitis in Rabbits," *Investigative Ophthmology*, vol. 13, No. 6, pp. 414-421, submitted Dec. 11, 1973.
"What should I expect before, during, and after surgery?" Last accessed Oct. 18, 2010.
"What is Lasik?" Last accessed Oct. 18, 2010.
"What are the risks and how can I find the right doctor for me?" Last accessed Oct. 22, 2010.

* cited by examiner

*Primary Examiner* — Trevor Love
(74) *Attorney, Agent, or Firm* — Dickstein Shapiro LLP

(57) ABSTRACT

The present invention relates to a pharmaceutical formulation comprising xanthan gum as a re-epithelializing active principle optionally mixed with hyaluronic acid. The composition speeds up and improves advantageously the formation of newly grown epithelium.

2 Claims, No Drawings

RE-EPITHELIALIZING PHARMACEUTICAL COMPOSITIONS COMPRISING XANTHAN GUM

This application is the U.S. National Phase of International Application PCT/IT03/00257, filed on Apr. 24, 2003 and claims priority to European Patent Office Foreign Patent Application Nos. 02425274.4, filed Apr. 30, 2002.

FIELD OF THE INVENTION

The present invention relates to re-epithelializing pharmaceutical compositions especially for ophthalmic use.

BACKGROUND ART

It is well known that epithelial cells, for example in the cornea, may suffer injuries caused by foreign bodies, such as abrasions, cuts and wounds (accidental, surgical, immunological etc), and postinfective ulcers. Injuries of this sort generally require long wound healing periods; cause much discomfort and often an imperfect wound closure.

SUMMARY OF THE INVENTION

The object of the present invention is a pharmaceutical composition that can accelerate re-epithelialization, especially of the corneal tissue, and is also well tolerated.

This goal is achieved using xanthan gum for the preparation of a medication for the treatment of epithelial wounds, as well as of pharmaceutical compositions containing xanthan gum, as detailed in the claims herewith annexed.

Other characteristics, and the advantages of the pharmaceutical topical composition, as described in the present invention, will become apparent from the following description of some preferred embodiments of formulations of the pharmaceutical composition, which are presented for purposes of illustration and are not intended to be construed as limiting.

DETAILED DESCRIPTION OF THE INVENTION

A surprising experimental finding was the observation that xanthan gum shows a high re-epithelializing function, that is to say, it is able to accelerate the formation of new epithelial cells at the level of the damaged epithelial zone, as shown also in an in vivo experiment reported later in the present description.

Xanthan gum is a heteropolysaccharide with a molecular weight between $3-7,5\times10^6$ Da, produced through a process of fermentation by the bacterium *Xanthomonas campestris.*

The primary structure of xanthan is a branched chain, with a main chain of $\beta(1\rightarrow4)$-D-glucose identical to cellulose wherein, a trisaccharide chain with a glucosidic link $\beta(1\rightarrow3)$, composed of acetylated mannose, glucuronic acid, and mannose is linked to every other second residue; finally, to each carbon C4 and C6 of the terminal unit of mannose a molecule of pyruvic acid is linked in a variable proportion of 25-50%, that completes the structure of the lateral chain of the polymer.

The available data suggests a single helix conformation (but a double or triple helical structure cannot be ruled out) where the lateral chains of the polymer tend to align with the main chain (with non covalent type of interactions) protecting the glucosidic links present there. The result is a stiff rod-like structure that confers great stability to the molecule with an excellent protection from strong acids and bases, high temperatures, freezing and thawing cycles, enzymatic attack, prolonged mixing, shear degradation, variations of ionic force and pH.

Consequently, on account of the structural properties just described, xanthan gum, in preformed gel form, makes it possible to carry out adequately the important function of mechanical protection.

Furthermore, following lot of experiments, it has been surprisingly observed that the admixture of xanthan gum with hyaluronic acid, as an active principle of a re-epithelializing composition in a preparation as a preformed gel, causes an increase in the rate of re-epithelializing of the damaged epithelium and, in addition, promotes the reorganization of the newly formed epithelium that results in the formation of cellular layer of superior quality.

In particular, wound-healing studies carried out under a scanning electron microscope, revealed a surprising degree of epithelial organization following a treatment with the pharmaceutical re-epithelializing composition according to the invention, as will be explained in detail.

It is well known that hyaluronic acid not only favors cellular proliferation but also stabilizes the basal layer of the epithelium stimulating the production of lamina and fibronectin.

In any event, when xanthan gum and hyaluronic acid are used as a mix in their capacity as re-epithelializing agents, they have a surprising synergic effect.

Hyaluronic acid is an high molecular weight polysaccharide with polyanionic features, high capacity to retain water, viscous, bioadhesive and pseudoplastic properties with no evidence of tixotropy. Its primary structure consists of $\beta(1\rightarrow4)$ disaccharide blocks each constituted of D-glucuronic acid and N-acetyl-D-glucosamine linked together through a $\beta(1\rightarrow3)$ bond.

In view of the observations previously described, a further embodiment of the present invention is to provide topical re-epithelializing pharmaceutical compositions in preformed gel consisting essentially of xanthan gum as active principle, eventually mixed with hyaluronic acid, and pharmacologically accepted additives.

The percentage of xanthan gum relative to the total volume of the preformed gel is preferably between 0.7% to 5%, more preferably between 0.8% and 3%, and more highly preferably between 0.9% and 1.5%.

The excipients are chosen among isotonic agents, buffers, solvents or vehicles, antioxidants, pH adjusting and similar.

In particular, the possible isotonic agents of the composition of the invention may be ionic, such as NaCl, KCl or non-ionic, for example glycerol, mannitol or a mix thereof.

Possible buffers may be those commonly used for instance in ophthalmic formulations such as phosphate or borate, acetate, a mix of these buffers such as citrate/phosphate, or even buffers not frequently used in the ophthalmic field, such as Tris.HCl, or based on histidine or arginine.

Therefore, the composition of a preformed gel with xanthan may be a balanced saline solution, or otherwise, o saline composition not necessarily balanced because of the presence of ions of $Ca^{+2}$ e $Mg^{+2}$.

Possible antioxidants include sodium citrate, ascorbate or sulfate.

Possible pH adjusting are organic or inorganic acids or bases with their respective acid and basic salts.

Possible solvents or vehicles are water or a mixture of water/oil.

It has been observed that when salts are added to a composition containing >0.25% xanthan, there is an increase of viscosity proportional to the concentration of xanthan and of the added salts, although a viscosity plateau is reached, for example, with as little as 0.1% of NaCl. Therefore, xanthan behaves differently toward the variations of ionic force than other polyelectrolytes, toward which the presence of salts (that decreases the degree of hydration and repulsion between chains) promotes intermolecular interaction and a molecular collapse from a random coil (with a higher viscosity) to a compact coil structure (with a lower viscosity). In xanthan solutions the addition of salts decreases the degree of hydration and the charge repulsion between the carboxylate anions of the lateral chains of the molecule, which consequently stabilizes the stiff rod-like conformation and promotes a stronger and more rigid three-dimensional network that increases viscosity (about twofold at 0.1% of NaCl for 1% xanthan) and significant yield-value, that in general render the solutions of the polymer more protected against factors such as thermal treatment, attacks from acids and bases, prolonged mixing, etc.

In solution, the single helixes tend to associate forming a complex ordered meshwork of rigid molecules held together mainly by weak Van der Waals forces. The effect of the distinctive and unique structure of xanthan in solution is, already for moderate concentrations (1-2.5%), a gel-like consistency with significant yield stress values (hence, excellent ability to favor the formation of suspensions and emulsions) and good viscosity.

Taken together, the properties thus far examined, along with the low toxicity, bioadhesiveness, and compatibility with the most common excipients and available commercial packaging render xanthan gum advantageously suitable also as delivery system as well as a protective agent on purely mechanical grounds.

As mentioned before, an additional embodiment of the present invention may include hyaluronic acid.

Specifically, the quantity of hyaluronic acid present in said composition ranges from 0.01% to 1% of the total volume of the preformed gel, preferably from 0.05% to 0.5%, better still from 0.1% to 0.4%. Hyaluronic acid is present as a salt. Possible counter ions may be, for example, sodium, potassium, calcium or magnesium.

In yet another embodiment of the present invention the re-epithelializing pharmaceutical composition may include, aside from the admixture of xanthan gum and hyaluronic acid as re-epithelializing agents, one or several pharmacological agents chosen among antiinfective, antiinflamatory, anesthetizing and mydriatic agents.

The invention is further disclosed by means of the following non limiting examples of same formulations.

FORMULATION 1

| Components | Quantity | Function |
|---|---|---|
| Xanthan gum | 1.0000 g | Active principle, re-epithelializing |
| Sodium chloride | 0.3500 g | Isotonic agent |
| Sodium phosphate, dibasic•12H$_2$O | 0.3638 g | Buffer |
| Sodium phosphate monobasic•H$_2$O | 0.0354 g | Buffer |
| Glycerol | 1.0000 g | Isotonic agent |
| Purified water q.s. to | 100.0 ml | Solvent |

FORMULATION 2

| Components | Quantity | Function |
|---|---|---|
| Xanthan gum | 1.0000 g | Active principle, re-epithelializing |
| Sodium chloride | 0.3500 g | Isotonic agent |
| Potassium chloride | 0.1500 g | Isotonic agent |
| Magnesium•chloride 6H$_2$O | 0.0120 g | Isotonic agent |
| Calcium chloride•2H$_2$O | 0.0084 g | Isotonic agent |
| Sodium phosphate dibasic•12H$_2$O | 0.0890 g | Buffer |
| Sodium phosphate monobasic•H$_2$O | 0.0069 g | Buffer |
| Sodium citrate•2H$_2$O | 0.0590 g | Buffer/antioxidant |
| Glycerol | 1.0000 g | Isotonic agent |
| Purified water q.s. to | 100.0 ml | Solvent |

FORMULATION 3

| Components | Quantity | Function |
|---|---|---|
| Hyaluronic acid sodium salt | 0.1500 g | Active principle, re-epithelializing |
| Xanthan gum | 1.0000 g | Active principle, re-epithelializing |
| Sodium chloride | 0.3500 g | Isotonic agent |
| Potassium chloride | 0.1500 g | Isotonic agent |
| Magnesium chloride•6H$_2$O | 0.0120 g | Isotonic agent |
| Calcium chloride•2H$_2$O | 0.0084 g | Isotonic agent |
| Sodium phosphate dibasic•12H$_2$O | 0.0890 g | Buffer |
| Sodium phosphate monobasic•H$_2$O | 0.0069 g | Buffer |
| Sodium citrate•2H$_2$O | 0.0590 g | Buffer/antioxidant |
| Glycerol | 1.0000 g | Isotonic agent |
| Purified water q.s. to | 100.0 ml | Solvent |

FORMULATION 4

| Components | Quantity | Function |
|---|---|---|
| Hyaluronic acid sodium salt | 0.1500 g | Active principle, re-epithelializing |
| Xanthan gum | 1.0000 g | Active principle, re-epithelializing |
| Sodium chloride | 0.3500 g | Isotonic agent |
| Potassium chloride | 0.1500 g | Isotonic agent |
| Magnesium chloride•6H$_2$O | 0.0120 g | Isotonic agent |
| Calcium chloride•2H$_2$O | 0.0084 g | Isotonic agent |
| Tris base | 0.2425 g | Buffer |
| HCl 1N q.s. to | pH 7.4-7.6 | Buffer |
| Sodium citrate•2H$_2$O | 0.0590 g | Buffer/antioxidant |
| Glycerol | 0.5000 g | Isotonic agent |
| Purified water q.s. to | 100.0 ml | Solvent |

FORMULATION 5

| Components | Quantity | Function |
|---|---|---|
| Netilmicin sulfate equivalent to | 0.4550 g | Active principle |
| Netilmicin base | 0.3000 g | |
| Sodium hyaluronate | 0.1500 g | Active principle, re-epithelializing |
| Xanthan gum | 1.0000 g | Active principle, re-epithelializing |
| Sodium chloride | 0.8700 g | Isotonic agent |
| Sodium hydroxide 1M q.s. to | pH = 7.00-7.6 | pH adjusting |
| Purified water q.s. to | 100.0 ml | Solvent |

FORMULATION 6

| Components | Quantity | Function |
|---|---|---|
| Netilmicin sulfate equivalent to | 0.4550 g | Active principle |
| Netilmicin base | 0.3000 g | |
| Sodium hyaluronate | 0.1500 g | Active principle, re-epithelializing |
| Xanthan gum | 1.0000 g | Active principle, re-epithelializing |
| Sodium phosphate dibasic dodecahydrate. | 0.5000 g | Buffer |
| Sodium phosphate monobasic monohydrate | 0.1465 g | Buffer |
| Sodium citrate dihydrate | 2.1000 g | Buffer/antioxidant |
| Purified water q.s. to | 100.0 ml | Solvent |

FORMULATION 7

| Components | Quantity | Function |
|---|---|---|
| Netilmicin sulfate equivalent to | 0.4550 g | Active principle |
| Netilmicin base | 0.3000 g | |
| Sodium hyaluronate | 0.1500 g | Active principle, re-epithelializing |
| Xanthan gum | 1.0000 g | Active principle, re-epithelializing |
| Tris base | 0.2425 g | Buffer |
| HCl 1M q.s. to | pH 7.4-7.6 | Buffer |
| Sodium citrate dihydrate | 2.1000 | Buffer/antioxidant |
| Purified water q.s. to | 100.0 ml | Solvent |

FORMULATION 8

| Components | Quantity | Function |
|---|---|---|
| Netilmicin sulfate equivalent to | 0.4550 g | Active principle |
| Netilmicin base | 0.3000 g | |
| Sodium hyaluronate | 0.1500 g | Active principle, re-epithelializing |
| Xanthan gum | 1.0000 g | Active principle, re-epithelializing |
| Tris base | 0.2423 g | Buffer |
| HCl 1M q.s. to | pH 7.4-7.6 | Buffer |
| Sodium chloride | 0.7000 g | Isotonic agent |
| Purified water q.s. to | 100.0 ml | Solvent |

FORMULATION 9

| Components | Quantity | Function |
|---|---|---|
| Dexamethasone disodium phosphate | 0.1500 g | Active principle |
| Xanthan gum | 1.0000 g | Active principle, re-epithelializing |
| Sodium phosphate dibasic•12H$_2$O | 0.5000 g | Buffer |
| Sodium phosphate monobasic•H$_2$O | 0.1465 g | Buffer |
| Sodium citrate•2H$_2$O | 2.1000 g | Antioxidant |
| Purified water q.s. to | 100.0 ml | Solvent |

FORMULATION 10

| Components | Quantity | Function |
|---|---|---|
| Dexamethasone disodium phosphate | 0.1500 g | Active principle |
| Netilmicin sulfate equivalent to | 0.4550 g | Active principle |
| Netilmicin base | 0.3000 g | |

FORMULATION 10 -continued

| Components | Quantity | Function |
|---|---|---|
| Xanthan gum | 1.0000 g | Active principle, re-epithelializing |
| Sodium phosphate dibasic•12H$_2$O | 0.5000 g | Buffer |
| Sodium phosphate monobasic•H$_2$O | 0.1465 g | Buffer |
| Sodium citrate•2H$_2$O | 2.1000 g | Antioxidant |
| Purified water q.s. to | 100.0 ml | Solvent |

In general, in the compositions of the invention, glycerol displays a dispersing action towards xanthan gum, preventing the formation of clumps and lumps during the dispersal phase of the polymer in H$_2$O.

A general description of a procedure for the preparation of a pharmaceutical composition in accordance with the present invention will now follow. By way of illustration, the formulation prepared is for 100 ml/g of product.

Procedure for the Preparation of a Preformed Re-Epithelializing Gel

In a volume of purified water of about 50 ml all the additives of the formulation are added and dissolved, adding each component after the preceding one has been completely dissolved.

If the composition requires it, a predetermined quantity of one or more of the pharmacological agents listed above is added to the solution until said pharmacological agent(s) is/are completely dissolved or mixed.

Separately, one gram of xanthan gum is added to 50 ml of water and is dispersed on the surface of the liquid, without stirring, to avoid the formation of lumps. Alternatively, the dispersion may be homogenized with a paddle stirrer or a homogenizer so as to accelerate the process while avoiding the formation of lumps. If the composition requires it, hyaluronic acid is also dispersed in this phase.

The homogeneous dispersion is then autoclaved until a minimum F0=15 valid for the sterility is obtained (lethality, expressed in terms of equivalent of time in minutes at a 121° C. temperature with reference to the killing of microorganisms during the process of steam sterilization).

A this point, the solution of the additives sterilized thorough filtration (if a suspension sterilize in suitable manner) is aseptically added to the xanthan gum dispersion and stirred for about 1 hr. at a speed that will allow for smooth mixing without excessive turbulence, until a homogeneous gel is obtained.

Finally, the gel may be aseptically distributed in the appropriate containers.

To illustrate the efficacy of the main compositions of the invention, two experiments will be describe that were carried out to verify, in an in vivo re-epithelializing model, the effect of 2 preformed gels according to the aforesaid formulations—one (Formulation 2) containing only xanthan gum (XNT) and another (Formulation 3) containing both xanthan gum and hyaluronic acid (EPG)—in comparison to a solution containing only 0.15% sodium hyaluronate and salts (EYP) and a saline solution with no polymers (SOL).

Re-Epithelialization Efficacy

The difference between the two experiments lies in the fact that the first is designed to asses the dynamic and quantitative aspects of re-epithelialization and the second to asses the morphological and qualitative aspects of re-epithelialization following treatment with the various formulations. In the first experiment a confocal ophthalmoscope (CSLO) was used to follow the re-epithelialization rate and in the latter a scanning electron microscope (SEM) was used for the ultrastructural analysis.

For each experiment New Zealand albino rabbits, subdivided in 6 treatment groups according to what is described in the next two paragraphs, were used Animals Male New Zealand albino rabbits (Charles River Italia), medium weight 2.400 Kg, were used.

The animals were allocated in animal rooms maintained in standard conditions of humidity (50%±10% RH) and temperature (19±2° C.) with alternating cycles of artificial light (12 hours darkness/light). The animals were fed and allowed water ad libitum.

Treatment Scheme and Regimen

After checking the eyes of the animals to exclude eventual ophthalmological pathologies, the animals were assigned to six different treatment groups according to the following scheme:

Animals used during the different observation and treatment times

|  | $T_0$ | $T_{24h}$ | $T_{48h}$ | $T_{72h}$ | $T_{96h}$ |
|---|---|---|---|---|---|
| Control | 4 | — | — | — | — |
| Untreated wound | 4 | 4 | 4 | 4 | 4 |
| EPG | 4 | 4 | 4 | 4 | 4 |
| XNT | 4 | 4 | 4 | 4 | 4 |
| EYP | 4 | 4 | 4 | 4 | 4 |
| SOL | 4 | 4 | 4 | 4 | 4 |

Legend
Control: animals with intact cornea not pharmacologically treated.
Untreated wound: animals with corneal wound not pharmacologically treated
EPG, XNT, EYP, SOL: animals with corneal wound treated with the different formulations All the tested substances were administered 5 times a day until the end of the experiment.

Experimental Model

The animals were anesthetized by an i.m. injection of ketamine (37.5 mg/kg b.w.) and xylazine (10 mg/kg b.w.), and with oxybuprocaine (1 drop/eye).

The corneal wound was executed using an Algerbrush with a 1 mm tip. With the aid of a sterile parafilm mask, with a 6 mm hole at the center, a circular area was de-epithelialized. The eye was immediately washed with sterile BBS to remove cell debris and the treatment was performed.

In time course the rabbits were evaluated at 0, 24, 48, 72 and 96 hours with a CLSO coupled to an image-processing system, or they were sacrificed for SEM analysis (0, 24, 48, and 72 hours).

The research method and results of each experiment are described hereafter.

CLSO Experiment

The eyes of the rabbits of each treatment group were treated with a 25 µl solution of 0.5% sodium fluorescein. After 2 minutes the excess of fluorescein was washed away with a physiological solution. The sedated rabbits were then examined through CLSO. This system detects the fluorescent signal that originates from the epithelium lacking damaged zone and measures quantitatively the damaged area through an image-processing system.

Results

The CLSO analysis revealed that the wound heals spontaneously after 72 hours in all the treated groups.

The group treated with the formulation containing only xanthan gum as active principle (XNT) showed an accelerated re-epithelialization process already 24 hours after the treatment. The wound's closure was at least 30% more advanced than in the groups "Untreated wound", EYP and SOL. A higher re-epithelialization rate (50% higher than the other groups) was observed 48 hours after the treatment in both the group treated with xanthan gum only (XNT) and the group treated with xanthan gum mixed with hyaluronic acid (EPG). There were no observed differences between the group treated with only sodium hyaluronate (EYP) and the groups SOL and "untreated wound".

SEM Experiment

At predetermined times (0, 24, 48, 72 hours from the beginning of treatment) the animals of the different treatment groups were sacrificed (Tanax i.v.). Rapidly following the sacrifice the bulb was enucleated and the corneas excised and immediately fixed with 2% glutaraldehyde during 24 hours. Following fixation the corneas were processed for SEM analysis.

Results

All the corneas processed for observation immediately after corneal de-epithelialization ($T_0$) exhibit wounds with sharp raised margins and naked stroma. The controls (intact corneas) exhibit an homogeneous epithelium with a good degree of cellular differentiation, and a normal presence of "holes" (circumscribed areas lacking microvilli that are present on the surface of the epithelial cells with probable communication functions), serrated cellular contacts and numerous microvilli, presence of superficial epithelium with the typical mosaic aspect that reflects the different maturation stages (dark, medium light and light cells).

T24 Ore

Twenty four hours after the beginning of the experiment, the corneas of the group "Untreated wound" exhibit a de-epithelialized area with an entirely naked stroma, with the margin of the epithelium lacking zone sharp but hardly raised. All the newly formed cells present at the margins of the "wound" or slightly outside show few microvilli, and are not clearly differentiated into dark, medium and light.

The margins of the wounds of the corneas of the SOL group are similar to those of the preceding group, but the newly formed cells are more differentiated, with the presence of the three differentiation stages, and more profuse microvilli. Moreover, the cells are centripetally elongated, in contrast to the samples taken from the "Untreated wound" group, where the oblong shape is less evident.

In the corneas of the EYP group the margin of the epithelium-deprived zone is flattened and circumscribed by a ring of differentiated newly formed cells with a centripetally elongated aspect.

The corneas of the XNT group have an aspect to a large extent similar to those of the EYP group.

The corneas in the EPG group exhibit a flattened wound margin with cells with microvilli more numerous than in the other treatment groups. The newly formed cells exhibit a fair number of "holes".

T 48 Ore

The corneas of the "Untreated wound" group observed after 48 hours at the lowest magnification, exhibit a quite disorganized de-epithelialized zone, with marked and indented margins, and newly formed cells with partially enlarged junctions. A small number of cells are elongated and the small number of microvilli is short and distributed uniformly with no differentiation between light, medium and dark cells.

The samples of the SOL group also exhibit a de-epithelialized zone with quite irregular contours with marked margins, although the newly formed cells appear more differentiated, and the microvilli more numerous with virtually normal shape. The edges of the cells bordering the margins of the re-epithelialized zone are enlarged and in some cases raised.

The corneas of the EYP group re-epithelialized similarly to the corneas of the other groups. However, the contours of the de-epithelialized zone remain irregular, even if the degree of differentiation, the distribution and the quality of the microvilli of the newly formed cells is good.

The samples from the XNT treatment group exhibit irregular wound contours, but the state of the newly formed epithelium is notably better than that of the other groups. The new epithelium zone at the proximities of the wound margins presents a ring of centripetally elongated cells. Moreover, the degree of cellular differentiation, as well as the cellular contours are good, although zones where the cells appear raised in part persist. The microvilli are normal and numerous.

The organization of the samples of the EPG treatment group is similar to that of groups EYP and XNT. However, the edge of the wound, as in the previous observation time, is still flat. Consequently, the newly formed zone with centripetally oriented cells is larger, and in general, even at the lowest magnification, the aspect of the de-epithelialized zone is more uniform.

T 72 Ore

After 72 hours of treatment all the groups exhibit a healed wound, although small, spottily-distributed areas barren of cells and with enlarged junctions persist. This phenomenon is part of the normal re-epithelialization process and is caused by the continuous rearrangement of the newly formed epithelium.

The differences between the groups lie in the organization of the newly formed epithelium. In fact, in the "Untreated wound" group the epithelium appears uniform because of the presence of short and scant microvilli that give the epithelium a "pasty" appearance. Thus, the typical dark, medium and light cell differentiation is not present, except in the zones of newly formed epithelium more distant from the center, probably because in those zones the cellular turnover has returned to normal, while at the center cellular multiplication is still chaotic.

A certain degree of epithelial organization is exhibited by the SOL samples. In fact, even at the central zone, re-epithelialized later, a hint of differentiation is present, and in comparison to the corneas of the "Untreated wound" group, the microvilli are more numerous and "not-pasty".

The differences between the groups treated with the products containing biopolymers persist even at 72 hours, although the corneas treated with EPG are better that those treated with XNT, and the latter are better than those of the EYP group. In general the aspect of the corneas treated with EPG is similar to that of the controls (intact corneas), with numerous and long microvilli, a fair number of holes uniformly distributed in the cellular layer, and a good representation of cells at the diverse differentiation stages.

According to what has been described so far, the re-epithelializing pharmaceutical composition in preformed gel form accelerates the reconstruction of the damaged epithelium.

Moreover, said composition advantageously favors the reorganization of the epithelium and consequently increases the adhesion and stability of the new epithelium in the underlying connective tissue.

A further advantage of the composition, according to the present invention, is its formulation as a preformed gel as a consequence of which the re-epithelializing pharmaceutical composition also performs a mechanically protective function.

Preferably, when the composition of the invention includes the sodium salt of hyaluronic acid, its formulation exhibits extremely favorable characteristics for a product of topical use.

In particular, the consistency is that of an almost transparent, light cream colored, pleasant to the touch, non-sticky, easily spreadable and absorbed soft gel. The sensations upon instillation are similar: the preparation does not burn, the "blurry vision" sensation is very limited o non-existent while that of freshness and lubrication of the eye persists. Additionally, the product is easily administered both in terms of release from the container (ease of drop formation and delivery) and distribution of the drops on the ocular surface.

Furthermore, it was surprisingly observed that hyaluronic acid, although present in water at concentrations almost seven times lower than that of xanthan gum, has notable stabilization ability with respect to the conformation of the latter.

In fact, the viscosity of xanthan gum solutions without salts decrease in about 30% following thermal treatment.

On the contrary, the viscosity of xanthan gum solutions and hyaluronic acid sodium salt decreases only in 10-15% after thermal treatment.

In particular, the study of the rheological characteristics of the product has given the following results.

As an illustration, the viscosity/shear rate ($\eta/\gamma$) diagram of a composition consisting of 1% xanthan gum+hyaluronic acid was studied and compared to a composition of 1% xanthan+saline solution (BSS) and 1% xanthan+$H_2O$.

The rheological profile of the complete product presents very high $\eta$ (viscosity) and well-defined shear stress at low $\gamma$, and therefore, good strength, reticule consistency, and retention at the site of application. Viscosity ($\eta$) decreases rapidly as shear rate increases with a high degree of pseudoplasticity that confers good spreadability and distribution to the system at the application site, and gives the user a comfortable sensation. The $\eta/\gamma$ curve obtained by gradually increasing the shear rate coincides with that of the reverse path, obtained by gradually diminishing it; therefore, the system presents no tissuetropy and reacquires its structure instantaneously upon cessation of the shear stress.

In particular for ocular applications, this translates itself advantageously in the recovery of the structure and viscosity of the product between blinks consequently increasing the time of corneal contact.

As may be assessed from what has been described herewith, a re-epithelializing pharmaceutical composition according to the present invention answers to the needs mentioned in the introductory section and overcomes the shortcomings of the current state of the arts.

Obviously an expert in the field, in order to satisfy contingent and specific requirements may introduce numerous modifications and variations to the above-described composition, without departing from the scope of the invention as defined by the following claims.

What is claimed is:

1. A pharmaceutical re-epithelializing composition consisting of:
   0.15 weight % hyaluronic acid sodium salt as active principle,
   1.0 weight % xanthan gum as active principle,
   0.35 weight % sodium chloride as isotonic agent,
   0.15 weight % potassium chloride as isotonic agent,
   0.012 weight % magnesium chloride.$6H_2O$ as isotonic agent,
   0.0084 weight % calcium chloride.$2H_2O$ as isotonic agent,
   0.089 weight % sodium phosphate dibasic.$12H_2O$ as buffer, 0.0069 weight % sodium phosphate monobasic.H$_2$O as buffer,
0.059 weight % sodium citrate.2H$_2$O as buffer and antioxidant,
1.0 weight % glycerol as isotonic agent, and
purified water as solvent,
wherein the composition is effective for re-epithelialization when applied to epithelium; and
the xanthan gum and isotonic agent provide recovery of the structure and viscosity of the composition between blinks resulting in increased time of corneal contact.

2. A pharmaceutical re-epithelializing composition consisting of:
0.455 weight % netilmicin sulfate as active principle,
0.3 weight % netilmicin base,
0.15 weight % sodium hyaluronate as active principle,
1.0 weight % xanthan gum as active principle,
0.5 weight % of sodium phosphate dibasic dodecahydrate as buffer,
0.1465 weight % sodium phosphate monobasic monohydrate as buffer,
2.1 weight % sodium citrate dihydrate as buffer and antioxidant, and
purified water as solvent,
wherein the composition is effective for re-epithelialization when applied to epithelium; and
xanthan gum and salt provide recovery of the structure and viscosity of the composition between blinks resulting in increased time of corneal contact.

* * * * *